Figure 1:
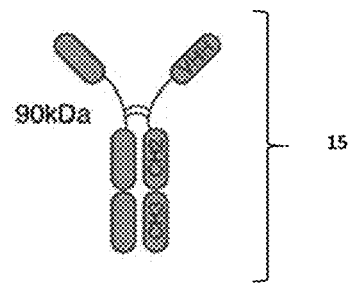

US010772945B2

(12) United States Patent
Fuener et al.

(10) Patent No.: US 10,772,945 B2
(45) Date of Patent: Sep. 15, 2020

(54) VHH CONSTRUCTS FOR DIVERTING AN IMMUNE RESPONSE

(71) Applicant: PRECLINICS GESELLSCHAFT FUER PRAEKLINISCHE FORSCHUNG MBH, Potsdam (DE)

(72) Inventors: Jonas Fuener, Potsdam (DE); Angelo Bolchi, Lesignano de' Bagni (IT); Erik Schliebs, Berlin (DE); Simone Ottonello, Parma (IT)

(73) Assignee: PRECLINICS GES. F. PRAEKLINISCHE FORSCHUNG MBH, Potsdam (DE)

( * ) Notice: Subject to any disclaimer, the term of this patent is extended or adjusted under 35 U.S.C. 154(b) by 0 days.

(21) Appl. No.: 15/562,901

(22) PCT Filed: Apr. 11, 2016

(86) PCT No.: PCT/EP2016/057892
§ 371 (c)(1),
(2) Date: Sep. 29, 2017

(87) PCT Pub. No.: WO2016/162553
PCT Pub. Date: Oct. 13, 2016

(65) Prior Publication Data

US 2018/0078632 A1 Mar. 22, 2018

(30) Foreign Application Priority Data

Apr. 10, 2015 (DE) ........................ 10 2015 105 487

(51) Int. Cl.

| | |
|---|---|
| *A61K 39/08* | (2006.01) |
| *A61K 39/235* | (2006.01) |
| *C07K 16/00* | (2006.01) |
| *C07K 16/46* | (2006.01) |
| *C07K 16/18* | (2006.01) |

(52) U.S. Cl.
CPC .............. *A61K 39/08* (2013.01); *C07K 16/18* (2013.01); *C07K 2317/22* (2013.01); *C07K 2317/569* (2013.01); *C07K 2319/40* (2013.01)

(58) Field of Classification Search
CPC .... A61K 39/08; C07K 16/18; C07K 2317/22; C07K 2317/569; C07K 2319/40
See application file for complete search history.

(56) References Cited

U.S. PATENT DOCUMENTS

| | | | | |
|---|---|---|---|---|
| 8,188,244 | B2 * | 5/2012 | La Monica | C07K 14/70503 536/23.1 |
| 2006/0263389 | A1 * | 11/2006 | Stacy | A61K 39/025 424/234.1 |
| 2008/0293636 | A1 * | 11/2008 | Cohen | C07K 16/2896 514/1.1 |
| 2010/0278830 | A1 | 11/2010 | Shoemaker et al. | |
| 2013/0058962 | A1 | 3/2013 | Shoemaker et al. | |

FOREIGN PATENT DOCUMENTS

EP 1790358 A1 5/2007

OTHER PUBLICATIONS

Muyldemans et al., Reviews in Molecular Biotechnology 74: 277-302 (Year: 2001).*
Rudikoff et al., Proc Natl Acad Sci USA 79 pp. 1979-1983 (Year: 1982).*
Wesolowski et al., Med Microbiol Immunol 198: 157-174 (Year: 2009).*
Patel et al., Protein Expression and Purification 75: 15-20 (Year: 2011).*
Abreu et al., Infection and Immunity 72(10): 5931-5937 (Year: 2004).*
Lederman et al., Mol Immunology 28(11): 1171-81 (Year: 1991).*
Colman et al., in Research in Immunology 145(1):33-36 (Year: 1994).*
Lloyd et al., Protein Engineering, Design & Selection 22:159-168 (Year: 2009).*
Edwards et al., J Mol Biol. 334(1): 103-118 (Year: 2003).*
Kubala et al., Structural and thermodynamic analysis of the GFP:GFP-nanobody complex, Protein Science 2010, vol. 19:2389-2401.
D'Huyvetter, M., et al., Targeted Radionuclide Therapy with A 177 Lu-labeled Anti-HER2 Nanobody, Theranostics, 2014, vol. 4, No. 7, pp. 708-720.
Gosling, JP., A Decade of Development in Immunoassay Methodology, Clinical Chemistry, 1990, vol. 36, No. 8, pt. 1, pp. 1408-1427.
Massa, S., et al., Site-Specific Labeling of Cysteine-Tagged Camelid Single-Domain Antibody-Fragments for Use in Molecular Imaging, Bioconjugate Chemistry, 2014, vol. 25, No. 5, pp. 979-988.
Mukherjee, J., et al., A Novel Strategy for Development of Recombinant Antitoxin Therapeutics Tested in a Mouse Botulism Model, Plos One, 2012, vol. 7, No. 1, pp. e29941.
Tillib, SV., et al., Single-domain antibody-based ligands for immunoaffinity separation of recombinant human lactoferrin from the goat lactoferrin of transgenic goat milk, Journal of Chromatography B: Biomedical Sciences & Applications, 2014, vol. 949, pp. 48-57.

(Continued)

*Primary Examiner* — Phuong Huynh
(74) *Attorney, Agent, or Firm* — Agris & Von Natzmer, LLP; Joyce Von Natzmer

(57) ABSTRACT

The invention relates to a novel VHH construct which can be bounded by a complete antibody without impairment of the antigen binding properties of the VHH construct being impaired. The invention also relates to an antibody construct comprising a VHH construct of this type and a kit, as well as the use thereof in immunodiagnostics or in the area of therapeutics. With the invention, among other things, it is possible to direct the existing immunity of a patient toward a different antigen.

15 Claims, 6 Drawing Sheets

Specification includes a Sequence Listing.

(56) References Cited

OTHER PUBLICATIONS

Tremblay, J., et al., A single VHH-Based Toxin-Neutralizing Agent and an Effector Antibody Protect Mice against Challenge with Shiga Toxins 1 and 2, Infection and Immunity, 2013, vol. 81, No. 12, pp. 4592-4603.

* cited by examiner

SEQUENCE LISTING

```
<160> NUMBER OF SEQ ID NOS: 18

<210> SEQ ID NO 1
<211> LENGTH: 210
<212> TYPE: PRT
<213> ORGANISM: Clostridium tetani

<400> SEQUENCE: 1

Thr Ser Tyr Leu Ser Ile Thr Phe Leu Arg Asp Phe Trp Gly Asn Pro
1               5                   10                  15

Leu Arg Tyr Asp Thr Glu Tyr Tyr Leu Ile Pro Val Ala Ser Ser Ser
            20                  25                  30

Lys Asp Val Gln Leu Lys Asn Ile Thr Asp Tyr Met Tyr Leu Thr Asn
        35                  40                  45

Ala Pro Ser Tyr Thr Asn Gly Lys Leu Asn Ile Tyr Tyr Arg Arg Leu
```

```
                    50                  55                  60
Tyr Asn Gly Leu Lys Phe Ile Ile Lys Arg Tyr Thr Pro Asn Asn Glu
 65                  70                  75                  80

Ile Asp Ser Phe Val Lys Ser Gly Asp Phe Ile Lys Leu Tyr Val Ser
                     85                  90                  95

Tyr Asn Asn Asn Glu His Ile Val Gly Tyr Pro Lys Asp Gly Asn Ala
                    100                 105                 110

Phe Asn Asn Leu Asp Arg Ile Leu Arg Val Gly Tyr Asn Ala Pro Gly
                    115                 120                 125

Ile Pro Leu Tyr Lys Lys Met Glu Ala Val Lys Leu Arg Asp Leu Lys
                130                 135                 140

Thr Tyr Ser Val Gln Leu Lys Leu Tyr Asp Asp Lys Asn Ala Ser Leu
145                 150                 155                 160

Gly Leu Val Gly Thr His Asn Gly Gln Ile Gly Asn Asp Pro Asn Arg
                    165                 170                 175

Asp Ile Leu Ile Ala Ser Asn Trp Tyr Phe Asn His Leu Lys Asp Lys
                180                 185                 190

Ile Leu Gly Cys Asp Trp Tyr Phe Val Pro Thr Asp Glu Gly Trp Thr
                195                 200                 205

Asn Asp
    210

<210> SEQ ID NO 2
<211> LENGTH: 23
<212> TYPE: PRT
<213> ORGANISM: Clostridium tetani

<400> SEQUENCE: 2

Gly Asn Pro Leu Arg Tyr Asp Thr Glu Tyr Tyr Leu Ile Pro Val Ala
 1               5                  10                  15

Ser Ser Ser Lys Asp Val Gln
                20

<210> SEQ ID NO 3
<211> LENGTH: 34
<212> TYPE: PRT
<213> ORGANISM: Clostridium tetani

<400> SEQUENCE: 3

Pro Ser Tyr Thr Asn Gly Lys Leu Asn Ile Tyr Tyr Arg Arg Leu Tyr
 1               5                  10                  15

Asn Gly Leu Lys Phe Ile Ile Lys Arg Tyr Thr Pro Asn Asn Glu Ile
                20                  25                  30

Asp Ser

<210> SEQ ID NO 4
<211> LENGTH: 36
<212> TYPE: PRT
<213> ORGANISM: Clostridium tetani

<400> SEQUENCE: 4

Asn Asn Glu His Ile Val Gly Tyr Pro Lys Asp Gly Asn Ala Phe Asn
 1               5                  10                  15

Asn Leu Asp Arg Ile Leu Arg Val Gly Tyr Asn Ala Pro Gly Ile Pro
                20                  25                  30

Leu Tyr Lys Lys
            35
```

```
<210> SEQ ID NO 5
<211> LENGTH: 16
<212> TYPE: PRT
<213> ORGANISM: Clostridium tetani

<400> SEQUENCE: 5

Gly Thr His Asn Gly Gln Ile Gly Asn Asp Pro Asn Arg Asp Ile Leu
1               5                   10                  15

<210> SEQ ID NO 6
<211> LENGTH: 18
<212> TYPE: PRT
<213> ORGANISM: Clostridium tetani

<400> SEQUENCE: 6

Lys Ile Tyr Ser Gly Pro Asp Lys Glu Gln Ile Ala Asp Glu Ile Asn
1               5                   10                  15

Asn Leu

<210> SEQ ID NO 7
<211> LENGTH: 23
<212> TYPE: PRT
<213> ORGANISM: Clostridium tetani

<400> SEQUENCE: 7

Gly Asn Pro Leu Arg Tyr Asp Thr Glu Tyr Tyr Leu Ile Pro Val Ala
1               5                   10                  15

Ser Ser Ser Lys Asp Val Gln
            20

<210> SEQ ID NO 8
<211> LENGTH: 34
<212> TYPE: PRT
<213> ORGANISM: Clostridium tetani

<400> SEQUENCE: 8

Tyr Asn Asp Thr Glu Gly Phe Asn Ile Glu Ser Lys Asp Leu Lys Ser
1               5                   10                  15

Glu Tyr Lys Gly Gln Asn Met Arg Val Asn Thr Asn Ala Phe Arg Asn
            20                  25                  30

Val Asp

<210> SEQ ID NO 9
<211> LENGTH: 37
<212> TYPE: PRT
<213> ORGANISM: Clostridium tetani

<400> SEQUENCE: 9

Ile Thr Leu Pro Asn Asp Arg Thr Thr Pro Val Thr Lys Gly Ile Pro
1               5                   10                  15

Tyr Ala Pro Glu Tyr Lys Ser Asn Ala Ala Ser Thr Ile Glu Ile His
            20                  25                  30

Asn Ile Asp Asp Asn
            35

<210> SEQ ID NO 10
<211> LENGTH: 20
<212> TYPE: PRT
<213> ORGANISM: Clostridium tetani

<400> SEQUENCE: 10
```

-continued

```
Arg Tyr Glu Phe Gly Thr Lys Pro Glu Asp Phe Asn Pro Pro Ser Ser
1               5                   10                  15

Leu Ile Glu Gly
            20

<210> SEQ ID NO 11
<211> LENGTH: 15
<212> TYPE: PRT
<213> ORGANISM: Clostridium tetani

<400> SEQUENCE: 11

Ala Gln Leu Val Pro Gly Ile Asn Gly Lys Ala Ile His Leu Val
1               5                   10                  15

<210> SEQ ID NO 12
<211> LENGTH: 19
<212> TYPE: PRT
<213> ORGANISM: Clostridium tetani

<400> SEQUENCE: 12

Ala Asn Lys Leu Ser Gln Val Thr Ser Cys Asn Asp Pro Asn Ile Asp
1               5                   10                  15

Ile Asp Ser

<210> SEQ ID NO 13
<211> LENGTH: 56
<212> TYPE: PRT
<213> ORGANISM: Human herpesvirus 4

<400> SEQUENCE: 13

Pro Arg Arg Pro Pro Gly Arg Arg Pro Phe Phe His Pro Val Gly
1               5                   10                  15

Glu Ala Asp Tyr Phe Glu Tyr His Gln Glu Gly Gly Pro Asp Gly Glu
                20                  25                  30

Pro Asp Met Pro Pro Gly Ala Ile Glu Gln Gly Pro Ala Asp Asp Pro
            35                  40                  45

Gly Glu Gly Pro Ser Thr Gly Pro
    50                  55

<210> SEQ ID NO 14
<211> LENGTH: 56
<212> TYPE: PRT
<213> ORGANISM: Human adenovirus type 2

<400> SEQUENCE: 14

Gly Gly Asn Asn Ser Gly Ser Gly Ala Glu Glu Asn Ser Asn Ala Ala
1               5                   10                  15

Ala Ala Ala Met Gln Pro Val Glu Asp Met Asn Asp His Ala Ile Arg
                20                  25                  30

Gly Asp Thr Phe Ala Thr Arg Ala Glu Glu Lys Arg Ala Glu Ala Glu
            35                  40                  45

Ala Ala Ala Glu Ala Ala Ala Pro
    50                  55

<210> SEQ ID NO 15
<211> LENGTH: 55
<212> TYPE: PRT
<213> ORGANISM: Human adenovirus type 2

<400> SEQUENCE: 15

Ala Ile Arg Gly Asp Thr Phe Ala Thr Arg Ala Glu Glu Lys Arg Ala
```

```
1               5                   10                  15
Glu Ala Glu Ala Ala Glu Ala Ala Ala Pro Ala Ala Gln Pro Glu
                20                  25                  30

Val Glu Lys Pro Gln Lys Lys Pro Val Ile Lys Pro Leu Thr Glu Asp
            35                  40                  45

Ser Lys Lys Arg Ser Tyr Asn
        50                  55

<210> SEQ ID NO 16
<211> LENGTH: 56
<212> TYPE: PRT
<213> ORGANISM: Human respiratory syncytial virus

<400> SEQUENCE: 16

Thr Gln Pro Ser Lys Pro Thr Thr Lys Gln Arg Gln Asn Lys Pro Pro
1               5                   10                  15

Ser Lys Pro Asn Asn Asp Phe His Phe Glu Val Phe Asn Phe Val Pro
                20                  25                  30

Cys Ser Ile Cys Ser Asn Asn Pro Thr Cys Trp Ala Ile Cys Lys Arg
            35                  40                  45

Ile Pro Asn Lys Lys Pro Gly Lys
        50                  55

<210> SEQ ID NO 17
<211> LENGTH: 359
<212> TYPE: PRT
<213> ORGANISM: Artificial Sequence
<220> FEATURE:
<223> OTHER INFORMATION: Fusionsprotein

<400> SEQUENCE: 17

Met Ala Gln Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
                20                  25                  30

Arg Tyr Ser Met Arg Trp Tyr Arg Gln Ala Pro Gly Lys Glu Arg Glu
            35                  40                  45

Trp Val Ala Gly Met Ser Ser Ala Gly Asp Arg Ser Ser Tyr Glu Asp
        50                  55                  60

Ser Val Lys Gly Arg Phe Thr Ile Ser Arg Asp Asp Ala Arg Asn Thr
65                  70                  75                  80

Val Tyr Leu Gln Met Asn Ser Leu Lys Pro Glu Asp Thr Ala Val Tyr
                85                  90                  95

Tyr Cys Asn Val Asn Val Gly Phe Glu Tyr Trp Gly Gln Gly Thr Gln
            100                 105                 110

Val Thr Val Ser Ser Glu Pro Lys Thr Pro Lys Pro Gln Pro Gln Pro
        115                 120                 125

Gln Pro Gln Pro Gln Pro Asn Pro Thr Thr Glu Ser Lys Cys Pro Thr
130                 135                 140

Ser Tyr Leu Ser Ile Thr Phe Leu Arg Asp Phe Trp Gly Asn Pro Leu
145                 150                 155                 160

Arg Tyr Asp Thr Glu Tyr Tyr Leu Ile Pro Val Ala Ser Ser Ser Lys
                165                 170                 175

Asp Val Gln Leu Lys Asn Ile Thr Asp Tyr Met Tyr Leu Thr Asn Ala
            180                 185                 190

Pro Ser Tyr Thr Asn Gly Lys Leu Asn Ile Tyr Tyr Arg Arg Leu Tyr
        195                 200                 205
```

```
Asn Gly Leu Lys Phe Ile Ile Lys Arg Tyr Thr Pro Asn Asn Glu Ile
    210                 215                 220

Asp Ser Phe Val Lys Ser Gly Asp Phe Ile Lys Leu Tyr Val Ser Tyr
225                 230                 235                 240

Asn Asn Asn Glu His Ile Val Gly Tyr Pro Lys Asp Gly Asn Ala Phe
                245                 250                 255

Asn Asn Leu Asp Arg Ile Leu Arg Val Gly Tyr Asn Ala Pro Gly Ile
            260                 265                 270

Pro Leu Tyr Lys Lys Met Glu Ala Val Lys Leu Arg Asp Leu Lys Thr
        275                 280                 285

Tyr Ser Val Gln Leu Lys Leu Tyr Asp Asp Lys Asn Ala Ser Leu Gly
290                 295                 300

Leu Val Gly Thr His Asn Gly Gln Ile Gly Asn Asp Pro Asn Arg Asp
305                 310                 315                 320

Ile Leu Ile Ala Ser Asn Trp Tyr Phe Asn His Leu Lys Asp Lys Ile
                325                 330                 335

Leu Gly Cys Asp Trp Tyr Phe Val Pro Thr Asp Glu Gly Trp Thr Asn
            340                 345                 350

Asp His His His His His His
        355

<210> SEQ ID NO 18
<211> LENGTH: 143
<212> TYPE: PRT
<213> ORGANISM: Artificial Sequence
<220> FEATURE:
<223> OTHER INFORMATION: Anti-GFP

<400> SEQUENCE: 18

Met Ala Gln Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
            20                  25                  30

Arg Tyr Ser Met Arg Trp Tyr Arg Gln Ala Pro Gly Lys Glu Arg Glu
        35                  40                  45

Trp Val Ala Gly Met Ser Ser Ala Gly Asp Arg Ser Ser Tyr Glu Asp
    50                  55                  60

Ser Val Lys Gly Arg Phe Thr Ile Ser Arg Asp Asp Ala Arg Asn Thr
65                  70                  75                  80

Val Tyr Leu Gln Met Asn Ser Leu Lys Pro Glu Asp Thr Ala Val Tyr
                85                  90                  95

Tyr Cys Asn Val Asn Val Gly Phe Glu Tyr Trp Gly Gln Gly Thr Gln
            100                 105                 110

Val Thr Val Ser Ser Glu Pro Lys Thr Pro Lys Pro Gln Pro Gln Pro
        115                 120                 125

Gln Pro Gln Pro Gln Pro Asn Pro Thr Thr Glu Ser Lys Cys Pro
    130                 135                 140
```

VHH CONSTRUCTS FOR DIVERTING AN IMMUNE RESPONSE

CROSS-REFERENCE TO RELATED APPLICATIONS

This is the U.S. national stage of International application PCT/EP2016/057892, filed Apr. 11, 2016 designating the United States and claiming priority to DE 10 2015 105 487.6, filed Apr. 10, 2015.

INCORPORATION OF SEQUENCE LISTING

The sequence listing was filed as a text file as part of International application PCT/EP2016/057892, filed Apr. 11, 2016 is hereby incorporated by reference. An extra copy of this text file named "7014-2040-SEQ-LIST-ST25", which is 12 kilobytes (measured in MS-WINDOWS), dated Sep. 29, 2017 was downloaded from WIPO, converted into ASCII format and renamed and is submitted herewith via the USPTO EFS system.

BACKGROUND OF THE INVENTION

In addition to conventional antibodies, each of which has two heavy and two light chains, camelids (old-world and new-world camels) also produce antibodies consisting exclusively of heavy chains. These so-called heavy-chain antibodies are homodimers of two identical heavy chains having a single variable domain for interacting with an antigen, known as VHH (variable domain of the heavy chain of heavy chain antibodies).

Thus camelids have IgG subclasses (IgG2+3) which have a VHH fragment instead of a Fab fragment. This VHH fragment offers various advantages in terms of antigen-binding behavior, but especially has the particular advantage of being able to be produced by a simple recombinant process in various expression organisms such as bacteria and yeasts. Likewise, antigen-binding VHH fragments can be produced synthetically. These recombinant VHH fragments are also known under the trade name of Nanobodies®.

The VHH domain has three complementarity-determining regions (CDRs) and four framework regions (FR). The VHH domain of a heavy chain antibody of this type forms a very small polypeptide unit characterized by a high antigen binding capacity, and therefore these fragments are of great interest for therapeutic and diagnostic purposes.

However, the VHH fragments cannot be used as complete antibodies, since the FC fragment is lacking. In therapeutic application this results in a shortened half life, and many laboratories do not have the appropriate secondary reagents for use in immune test systems such as ELISA.

In some instances the missing FC fragment is an advantage in use, but there are also applications in which coupling to an FC fragment would be advantageous. A human FC fragment is needed especially in immunotherapeutic applications. Problems often arise in the preclinical testing of antibody products, since the test product has a human FC fragment, but the preclinical studies were conducted in nonhuman organisms. The immune system responds very differently to FC fragments from other species. Therefore it would be advantageous if a new therapeutic agent in preclinical testing would be equipped with the respective FC fragment of the test species, but otherwise did not differ in any way from the product to be used in humans.

Monoclonal antibodies, most frequently monoclonal mouse antibodies, are often used in immune test systems. The development and production of monoclonal mouse antibodies is associated with great effort and expense. The preparation of recombinant and thus monoclonal VHH fragments can be done much more advantageously and efficiently. However, it would be advantageous for the immune test systems if an FC fragment of an antibody frequently used in such test systems were available in order to continue to work with the same protocols, reagents and methods.

To recreate complete immunoglobulins from the recombinantly produced VHH fragments, up to now the whole antibody was produced by recombinant means. In this process the Fab fragment is replaced by the VHH fragment. This method is primarily used for therapeutic purposes, and correspondingly, a human Fc fragment is used, as a rule. The production of such recombinant, chimeric antibodies can only be done in mammalian cells, and therefore the advantage of cost-advantageous, large-scale production of VHH fragments in bacteria or yeasts is lost.

VHH fragments are very small and on average have a molecular weight of about 12-15 kDa. VHH fragments as a medication have a very short plasma half-life unless modifications are made to prevent rapid renal clearance. For this purpose either serum protein linkers (e. g., HSA) may be used, or the entire construct can be enlarged by preparing bivalent or multivalent constructs. Another possibility is PEGylation of the protein.

VHH fragments are also used for research. Here they offer the advantage of being very small. Precisely for this reason, specially labeled VHH fragments are a valuable tool, particularly in live cell imaging. However, they are not usable for many immunologic detection methods, since either corresponding secondary reagents do not exist at all, or they are not available for the specific purpose.

DESCRIPTION OF THE INVENTION

Therefore the goal of the invention was to supply a VHH fragment that can be functionally integrated into immunoglobulins of other species. In particular, the possibility is to be disclosed of using VHH fragments from cost-advantageous fermenter production for the construction of chimeric immunoglobulins.

This goal is accomplished by the features of the independent claims. Particularly preferred embodiments can be found in the dependent claims.

In a first, preferred embodiment, the invention relates to a VHH construct comprising a VHH fragment and a protein tag, wherein the protein tag comprises one or more epitopes for binding an antibody, characterized in that the antigen binding properties of the VHH fragment remain essentially unchanged by the binding of the antibody to the protein tag.

When the VHH construct is bound to a complete antibody, the paratope of the VHH fragment thus replaces the paratope of the immunoglobulin, accompanied by changes in the binding properties, affinity and specificity.

A VHH fragment is also known as a single-domain antibody or nanobody. A VHH fragment comprises a single, monomeric variable domain of an antibody. VHH fragments in the meaning of the invention preferably consist of monomeric variable domains of heavy chain antibodies produced by representatives of the camel family and by cartilaginous fishes. Single-domain antibodies can also be obtained by monomerizing the dimers of variable domains of conventional antibodies of other species such as mouse or human by genetic engineering techniques.

It was surprising that the advantages of the VHH single domain antibodies are maintained by coupling with a protein tag. The VHH constructs of the invention likewise have good stability and along with high solubility, have other good properties for tissue penetration. In addition, they have high antigen specificity and good antigen-binding properties.

The invention also relates to the use of antibodies against (camelid) VHH fragments as carriers for these VHH fragments. The VHH fragments are coupled to the antibodies via a protein tag. The invention therefore relates to the use of antibodies as carriers of VHH fragments so they can be used like the usual antibodies. Preferred areas of application are research on and diagnosis and treatment of various diseases, e.g., cancer, infectious diseases or autoimmune diseases.

The antibodies directed against the protein tag, with the VHH constructs that they bind, form a new antibody construct which uses the paratope of the VHH fragment as a binding side against an antigen. In this way VHH fragments or Nanobodies® can easily be converted to a complete antibody-like construct. In this process the FC part preferably originates from the respective host organism of the anti-VHH antibody (e. g., mouse, rabbit, human) and he VHH fragments or the Nanobodies® are bound to the Fab fragment and can bind the target antigen with their binding site without impairment.

In the meaning of the invention, the statement that the binding of the antibody to the protein tag leaves the antigen binding properties of the VHH fragment essentially unchanged means that the VHH fragment can still bind specifically to the respective antigen. This is achieved in that the protein tag binds to the VHH fragment so that the paratope of the VHH fragment is not blocked. This is preferably accomplished in that the protein tag is located on the C-terminus of the VHH fragment.

An essential advantage of the invention lies in the use of the protein tag. By coupling the antibody to the VHH fragment via protein tags it becomes possible to maintain the functionality of the VHH fragment. On the other hand, when the antibody is coupled directly to the VHH fragment, the antigen-binding property is impaired so that the later applications cannot be performed or can only be performed with insufficient specificity. This is due to the fact, among other things, that the VHH fragments are very small. When antibodies bind directly to these, the antigen binding site is usually blocked or modified in such a manner that antigen binding is no longer possible. Another problem is that the antibody binding site is often no longer free when the VHH fragment has already bound to the antigen.

Therefore according to the invention the VHH fragments are provided with immunogenic peptide sequences (protein tags, which in the meaning of the invention are also called immunotags), in order to form, in combination with secondary antibodies to these peptide sequences, a novel construct combining the properties of both antibodies.

An additional advantage of this combination consists of the fact that the protein tags remain constant and, in particular, are independent of the respective VHH fragment. As a result, it is always possible to work with the same secondary antibodies for in vitro applications, and thus the costs can be reduced. In addition, use in immunoprecipitation, for which bivalent antibodies are needed, becomes possible. Monovalent VHH fragments or similar fragments cannot be used for these methods without further efforts, since this method is based on the aggregation of antibodies and antigens by crosslinking. Detection of VHH fragments is relatively difficult because of their small size and variability. These problems can be overcome by the invention.

At the same time, in the case of in vivo use within the body, independent of the species, utilization can be made of antibodies directed against the protein tags which are already present, for example, as a result of standard immunization or can be produced without problems in this way. It is important for the effector function of the endogenous antibodies to be maintained.

According to the invention, the antibodies should be bound to the VHH constructs in such a manner that the binding sites of the VHH fragments or nanobodies remain free. Thus the VHH fragment replaces the binding characteristics of the carrier antibody (also designated in the following as VHH carrier or carrier antibody), but in this process the basic framework of the binding antibody of the respective species is maintained, complete and unchanged. In this way the functionality of a VHH fragment can be combined with the properties of an immunoglobulin, especially the FC region-mediated effects, of various species. Thus VHH fragments can readily be incorporated into an existing diagnostic method. It is also possible to produce, for therapeutic applications, conjugates with the immunoglobulin of the target species, so that a number of application possibilities can be created.

It is particularly preferred for the protein tag to comprise at least two epitopes for binding an antibody. This embodiment has proven particularly advantageous, since the use of several epitopes can generate a diverse, polyclonal immune response or antibody binding. The epitopes used are preferably approximately 8 to 20, particularly preferably 10 to 15 amino acids long. Thus a preferred protein tag of the invention is at least 16, preferably at least 20, particularly preferably at least 30 amino acids long. The size of the protein tag is limited, since in each case only one antibody per protein tag should bind. Otherwise crosslinking without the antigen would take place, so that the therapeutic and diagnostic applications could no longer function.

It is particularly preferred for the protein tag to be located opposite the antigen binding site of the VHH fragment. This embodiment has proven advantageous since in this way it is possible to prevent the antigen binding properties of the VHH fragment from being impaired by the protein tag or the antibodies bound to it.

It is also preferred for the protein tag to be an immunogenic antigen. This embodiment in particular is also advantageous for use in immunodiagnostics, since it facilitates the generation of antibodies that bind the protein tag.

It is also preferred for the protein tag to be derived from the sequence of tetanus toxin.

A protein tag comprising the amino acid sequence of the C-terminal receptor-binding domain of the tetanus toxin or a part thereof, or an amino acid sequence having more than 80%, preferably 90% sequence identity with this sequence or parts thereof, has proven particularly advantageous.

The use of the total C-terminal receptor binding domain from the heavy chain of the tetanus toxin as the protein tag has also proven especially advantageous.

Also preferred are protein tags comprising sequences of T-cell epitopes and/or B-cell epitopes of tetanus toxins.

It is particularly preferred for the protein tag to comprise one or more of the sequences Seq ID No 1 to 16 or consist of one or more of these sequences.

It is apparent to the person skilled in the art that within the sequences of protein tags disclosed here, a certain modification of the amino acid sequence is possible without compromising the binding capacity of the antibody to the protein tag. For example it may be possible to change the protein tag by exchanging 1, 2 or 3 amino acids. In general, any of the amino acid residues within the sequences may be replaced by another residue as long as the resulting protein tag can still be specifically bound by the respective antibody. In addition, 1, 2 or 3 amino acids within one of the sequences may be deleted or added by addition as long as the binding capacity of an antibody to the protein tag is not completely eliminated.

In a preferred embodiment of the invention the protein tag has an amino acid sequence that exhibits sufficient homology to one of the sequences Seq ID No 1 to 16 to be functionally analogous to one of these sequences. In the meaning of the invention at least 40% homology is necessary for this purpose. In the meaning of the invention, being functionally analogous to the amino acid sequences named means that the protein tag is bound by the same antibodies.

In another advantageous embodiment of the invention the protein tag has at least 60%, preferably 70%, especially 80%, particularly preferably 90% homology to the amino acid sequences Seq ID No 1-16 according to the invention.

Tetanus-vaccinated individuals have a high fraction of antibodies that bind protein tags derived from tetanus toxin. Therefore the immune response to the tetanus vaccine can be directed toward a different target by administration of a VHH construct with such a protein tag. On one hand this opens up new possibilities in cancer treatment, and on the other hand completely new possibilities are also created in combating infectious disease or autoimmune diseases. For example, it is preferred for VHH fragments to be used against tumor targets which, by way of the protein tag, redirect an immune response of the patient to these targets.

The medication represents an attempt to discover alternatives to antibiotics, since resistance is increasingly becoming a problem. Therefore VHH constructs according to the invention are a highly promising approach for developing new medications against bacteria of all types.

In addition it is preferred to select other protein tags, wherein the preferred protein tags are those against which many people already have antibodies. This may mean structures against which many people are usually immunized by immunization programs. Other particularly preferred sequences identified were Seq. ID No. 13 to 16. It was shown that especially large numbers of people have antibodies to these epitopes, so that these sequences are highly suitable for use as protein tags. Initial experiments confirmed that the sequences are also suitable as protein tags for other reasons, namely that they do not change the antigen binding properties of the VHH fragments and are also still bound by the respective antibodies when they are fused with a VHH fragment.

The protein tag derived from the sequence of tetanus toxin, however, can also be used advantageously in tetanus antisera. Tetanus antisera are used in human and veterinary medicine. Here also the VHH construct replaces the actual specificity of the antibodies and makes the anti-TT antibodies into VHH carriers. Thus a plurality of immunotherapeutic products can be produced at low costs on the basis of tetanus antisera.

It is also preferred for the protein tag to be linked with the VHH fragment directly or over a linker and/or a structural protein. Thioredoxin is preferably used as the structural or scaffold protein, since especially good results in terms of stability could be achieved with this. It is also preferred for the linker to consist of amino acids. This is particularly preferably a GS linker or Yol linker.

It is also preferred for the antibody that binds the protein tag to be a complete immunoglobulin of a noncamelid species, preferably a mouse immunoglobulin, a rabbit immunoglobulin or a human immunoglobulin. However, antibodies from any other noncamelid species may also be used. The person skilled in the art knows which species he can select for the respective application without himself performing an inventive step.

It is particularly advantageous if the VHH fragment of the VHH construct is a recombinant VHH fragment. In such a case the manufacturing may be conducted as a soluble protein in bacteria, yeasts or mammalian cells. Particularly preferred is the production of the VHH fragments in cost-advantageous fermenter production. A person skilled in the art knows how a VHH domain can be produced by recombinant methods without himself performing an inventive step in the process.

It is also preferred for the entire VHH construct to be produced recombinantly. If the VHH fragment is produced recombinantly, it is possible to add an immunogenic epitope as a protein tag and produce the complete fusion protein recombinantly. In this way a larger distance between epitope and paratope on the VHH fragment can be achieved, which is advantageous to maintain the antigen binding properties.

Since the VHH fragments can also be obtained from synthetic libraries, the entire production process can take place in vitro, which is a significant advantage especially in the case of dangerous infectious pathogens, since the immunization of animals is often scarcely possible for safety reasons.

It is also preferred for the protein tag to be able to generate a polyclonal immune response in vivo.

It is also preferred for the protein tag to respond to patient immunoglobulins which either exist naturally or are induced in patients by vaccination.

In an additional preferred embodiment, the invention relates to a VHH construct described above for redirecting the immune response of a patient against one or more epitopes of the protein tag to the antigen that binds the VHH fragment. The patient antibodies are directed to a new target via the VHH construct. Thus a strong immune response is available immediately, even during the initial contact with the new antigen or an antigen against which the body does not produce an antibody.

In an additional preferred embodiment, the invention relates to an antibody construct comprising one or more previously described VHH construct and one or more antibodies, wherein the antigen binding properties of the VHH construct remain essentially unchanged by the binding of the antibody to the VHH construct. This involves a conventional antibody of noncamelid species with a VHH binding site as the antigen binding site. It is preferred for the antibody construct to comprise two VHH constructs, so that both antigen binding sites of the antibody are replaced by VHH constructs.

Thus the invention also relates to a chimeric immunoglobulin comprising one or more recombinantly produced VHH fragments and a complete immunoglobulin of a non-camelid species, wherein the VHH fragment and the immunoglobulin are bound together via a protein tag. It is preferred that the immunoglobulin binds to the VHH fragment via the protein tag without limiting the functionality of the VHH fragment.

One problem in the prior art is the insufficient stability and short half-lives of individual VHH chains. This problem was solved particularly well by an antibody construct. Distinctly prolonged half lives could be achieved by linking a VHH construct with a complete antibody.

In an additional preferred embodiment, the invention relates to a kit comprising one or more previously described VHH constructs and an antiserum comprising antibodies that bind the VHH construct to the protein tag.

Particularly preferred is a previously described VHH construct, antibody construct and/or kit for use as a medicinal product. The medicinal product may be a medication for cancer therapy or for combating infectious diseases or autoimmune diseases. Additional examples of applications are use against the acute coronary syndrome or rheumatoid arthritis.

Here it is preferred that the recombinant VHH fragments with the appended epitope, preferably a vaccine epitope, be administered to the patient. The VHH carrier against the epitope forms in the blood or plasma of the patient. The native antibodies bind the VHH construct and in this way achieve new reactivity determined by the VHH fragment. These VHH carriers can be used either for opsonization or also for blocking of epitopes in the patient.

Also particularly preferred is a previously described VHH construct, antibody construct and/or kit for diagnostic use.

The same principle according to the invention is applied for preferred use in clinical diagnostics. Here, however, it is advantageous to use protein tags in which no interferences with patient antibodies occur. It follows from this that protein tags against which many people already have antibodies are not suitable. In such cases it is preferred that a protein tag comprising a thioredoxin scaffold and an immunogenic peptide be used.

In an additional preferred embodiment, the invention relates to the use of one of the above-described VHH constructs, antibody constructs and kits for immunodiagnostics, preferably immunoprecipitation.

Some advantages of the invention for use in immunoprecipitation have already been described in the preceding. For this use, antisera are produced by means of immunogenic antigens. The preparation of antisera is improved and simplified according to the prior art, since these are now directed against an immunogenic antigen (and thus later protein tag). No weakly immunogenic antigens or antigens that are problematic for other reasons must be used. The use of protein tags makes it possible for the antigens for producing the antisera to be selected independently of the respective target antigens of the VHH fragments, which represents an enormous advantage.

Immunoprecipitation with VHH fragments entails numerous problems in the prior art. These problems can be overcome by the invention. This is related on one hand to the fact that the matrix dependence no longer exists to the same extent as in the prior art. Since it is now only necessary to produce an antiserum against the protein tag and then add the different VHH fragments against the antigens to be detected, different parameters may be measured in a matrix. The preparation may be conducted in larger batches, resulting in the obtainment of more uniform products than is the case in the prior art. This is especially important, since antisera usually can hardly be processed further. The quality of the antisera obtained is therefore of particular significance for the final product. Therefore, consistent quality can be achieved through this embodiment of the invention.

Since the VHH fragments can be produced recombinantly, there are no problems with achieving an adequate titer. A person skilled in the art is capable of selecting a suitable ligand to produce a corresponding antiserum.

In addition, for producing the antiserum for use in immunoprecipitation, it is advantageous if it can be selected such that no reaction occurs in the plasma of the production organism. This can be accomplished in that the protein tag and thus the antiserum can be selected and not determined by the target antigen of the VHH fragments.

Through the use of protein tags, VHH single-domain antibodies can ultimately also be used in immunodiagnostics, preferably immunoprecipitation, without deviating from existing protocols for the use of IgG products. The advantage lies in the fact that the functionality is similar to that of normal antibody products and therefore no adaptation of apparatus and protocols is necessary.

Satisfactory protein crosslink crosslinking can be achieved through the use of the invention. One problem in the prior art of immunoprecipitation is the frequent need for the use of antigens that have insufficient immunogenicity. This leads to problems in producing the antisera. This problem is eliminated if the protein tags are used in conjunction with VHH fragments in the sense of the invention. In this manner an animal, for example a sheep, a mouse or a horse, can be immunized with nonproblematic protein tags, rather than in the usual manner with potentially problematic or poorly immunogenic antigens. The obtainment of secondary antibodies is thus made simpler and more efficient and can also be standardized.

This protein crosslink crosslinking can then be measured. It is preferred for the evaluation to be performed using nephelometry. With this type of evaluation, the VHH constructs and antibody constructs provide especially good results even in a high-throughput arrangement. For immunodiagnostics, the functionality of the constructs according to the invention is comparable to that of normal antibody products, so that the FC fragment also contributes to the scattering during nephelometry.

In an additional preferred embodiment, the invention relates to a method for integrating a previously described VHH construct into an immunoglobulin of a noncamelid species, wherein the antigen binding site of the VHH fragment is not impaired.

The valence of the binding between immunoglobulin and VHH fragment must meet the requirements for the respective application. This is done, if possible and necessary, through established methods for protein crosslink crosslinking.

In an additional preferred embodiment, the invention relates to the use of an antibody with an FC moiety as carrier of a VHH construct comprising a VHH fragment and a protein tag, wherein the antibody binds to the protein tag and the antigen binding properties of the VHH fragment remain essentially unchanged by the binding of the antibody to the protein tag.

The following peptides are particularly suitable for use as the protein tag:

Particularly preferred is the use of the sequence of the C-terminal receptor-binding domain of tetanus toxin. Particularly preferably this involves the sequence Seq ID No. 1:

TSYLSITFLRDFWGNPLRYDTEYYLIPVASSSKDVQLKNITDYMYLTNAP

SYTNGKLNIYYRRLYNGLKFIIKRYTPNNEIDSFVKSGDFIKLYVSYNNN

EHIVGYPKDGNAFNNLDRILRVGYNAPGIPLYKKMEAVKLRDLKTYSVQL

KLYDDKNASLGLVGTHNGQIGNDPNRDILIASNWYFNHLKDKILGCDWYF

VPTDEGWTND

It is particularly preferred for one or more epitopes from the C-terminal receptor-binding domain of tetanus toxin to be selected for forming the protein tag. The following epitopes have proven particularly advantageous:

Seq ID No. 2:
GNPLRYDTEYYLIPVASSSKDVQ

Seq ID No. 3:
PSYTNGKLNIYYRRLYNGLKFIIKRYTPNNEIDS

Seq ID No. 4:
NNEHIVGYPKDGNAFNNLDRILRVGYNAPGIPLYKK

Seq ID No. 5:
GTHNGQIGNDPNRDIL

Epitopes from other domains of tetanus toxin can also be preferably used for producing the protein tag. It is particularly preferred for the protein tag to comprise one or more of the following sequences:

Seq ID No. 6:
KIYSGPDKEQIADEINNL

Seq ID No. 7:
GNPLRYDTEYYLIPVASSSKDVQ

Seq ID No. 8:
YNDTEGFNIESKDLKSEYKGQNMRVNTNAFRNVD

Seq ID No. 9:
ITLPNDRTTPVTKGIPYAPEYKSNAASTIEIHNIDDN

Seq ID No. 10:
RYEFGTKPEDFNPPSSLIEG

Seq ID No. 11:
AQLVPGINGKAIHLV

Seq ID No. 12:
ANKLSQVTSCNDPNIDIDS

Also advantageous is the use of a sequence from the EBNA-1 protein from human herpesvirus 4:

Seq ID No. 13:
PRRPPPGRRPFFHPVGEADYFEYHQEGGPDGEPDMPPGAIEQGPADDPGE
GPSTGP

Protein sequences from the capsid of human adenovirus 2 have also proven well suited as sequences in a protein tag:

Seq ID No. 14:
GGNNSGSGAEENSNAAAAAMQPVEDMNDHAIRGDTFATRAEEKRAEAEA
AAEAAAP

Seq ID No. 15:
AIRGDTFATRAEEKRAEAEAAAEAAAPAAQPEVEKPQKKPVIKPLTEDS
KKRSYN

Also advantageous is the use of a sequence from glycoprotein G of human RSV:

Seq ID No. 16:
TQPSKPTTKQRQNKPPSKPNNDFHFEVFNFVPCSICSNNPTCWAICKRI
PNKKPGK

Sequence ID Nos. 1 to 16 are particularly suitable for directing the immune response of patients to another antigen, since many people have antibodies against the above-mentioned sequences. In addition, these sequences can be used especially well for protein tags in the sense of the invention, since they can be appended to VHH fragments without impairing the antigen-binding characteristics of the VHH fragment. This means that preferred protein tags of the invention comprise or consist of one or more of the sequences mentioned.

EXAMPLES AND FIGURES

In the following, the invention will be explained on the basis of exemplified embodiments and figures, wherein these serve only to provide better clarity and are not intended to restrict the protective scope of the invention. The drawings are schematic representations, in which the size relationships were adapted for better clarity and do not correspond to reality.

FIGURES

Figure 2:
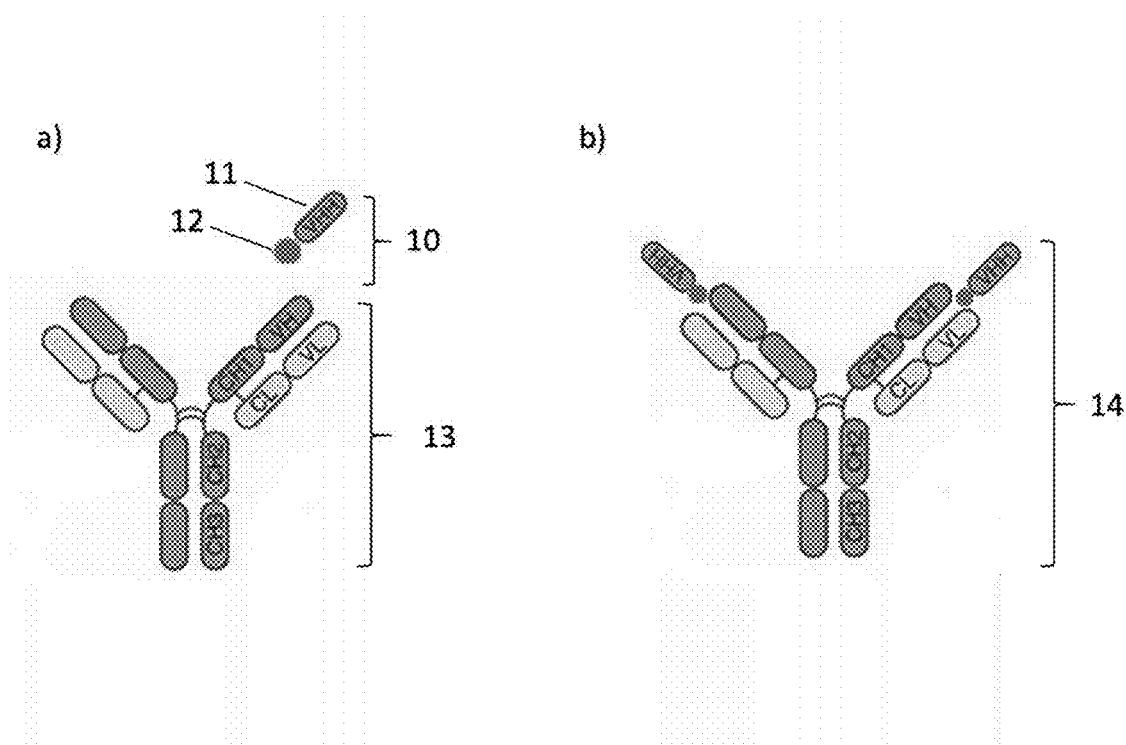
Figure 3:
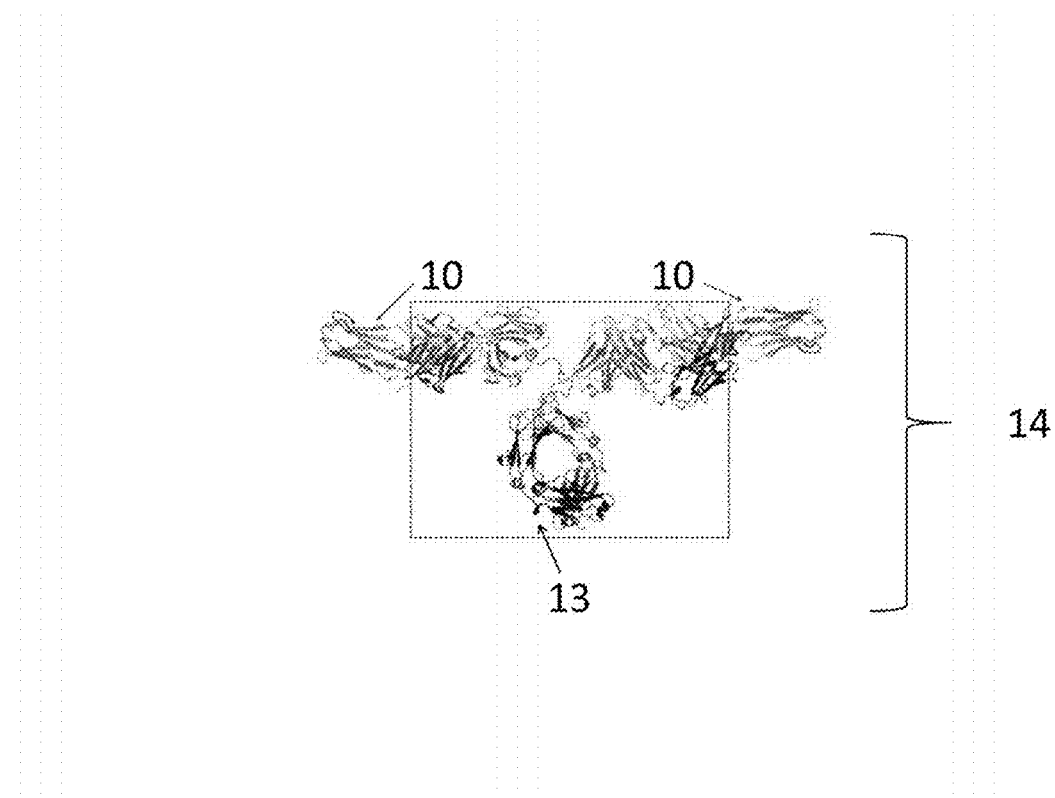
Figure 4:
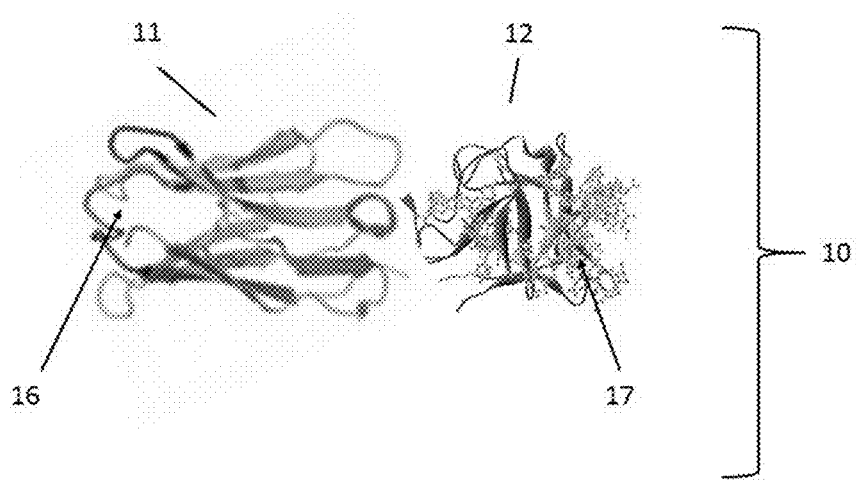
Figure 5:
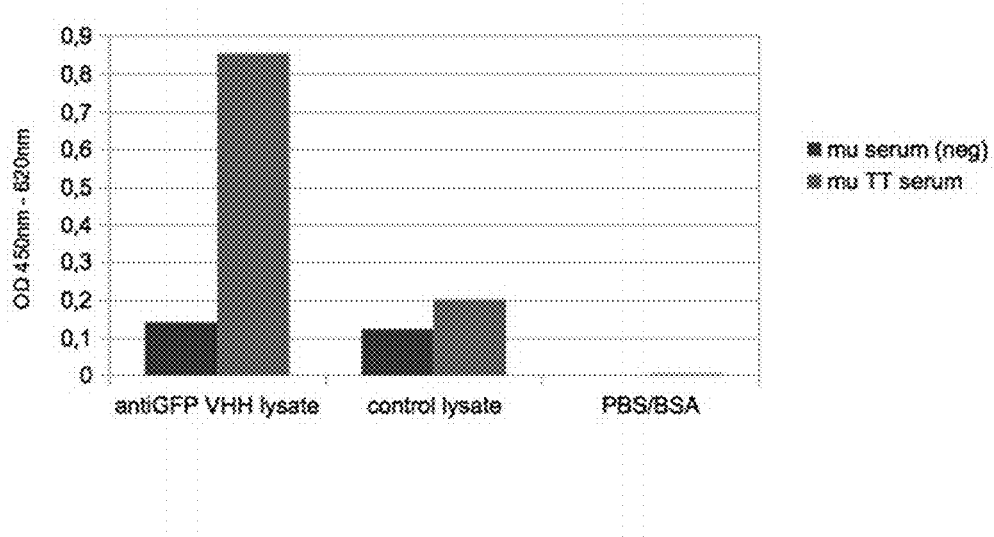
Figure 6:
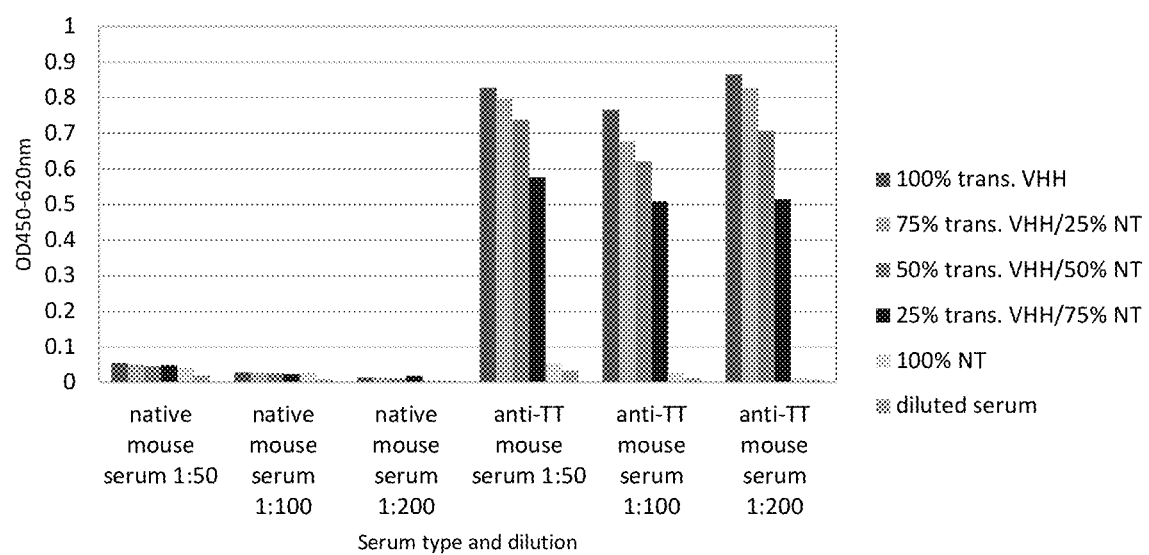

The figures show:
FIG. 1 a heavy chain antibody of a llama 15
FIG. 2a) a conventional antibody 13 and a preferred VHH construct 10 of the invention, and in FIG. 2B a preferred antibody construct 14 of the invention
FIG. 3 a preferred antibody construct 14 of the invention
FIG. 4 a preferred VHH construct 10 of the invention
FIG. 5 the result of an experiment with an anti-GFP VHH construct
FIG. 6 an additional result of an experiment with an anti-GFP VHH construct
Specifically:
FIG. 1 shows a conventional heavy chain antibody from a llama.
FIG. 2 is a schematic representation of a preferred antibody construct 14 of the invention, having two VHH constructs 10 of the invention.
FIG. 3 shows an antibody construct 14 of the invention, having two VHH constructs 10 of the invention bonded to it.
FIG. 4 shows the schematic representation of a VHH construct 10 of the invention, in which the size ratios of the VHH-Fragment 11 and the protein tag 12 do not correspond to reality, but have been modified for greater clarity. The left-hand part of the figure shows a VHH fragment 11 with an antigen binding site 16. The right-hand part of the figure shows a preferred protein tag 12 containing a sequence of the C-terminal receptor binding domain of tetanus toxin 17.
FIG. 5 shows how the tetanus response of mice immunized against tetanus can be redirected against GFP. The figure shows lysates of cells that produce VHH constructs. As the figure shows, the mouse IgG antibodies of tetanus-immunized mice can bind to GFP over a VHH construct. The tetanus immunity was able to be successfully redirected against GFP.
FIG. 6 shows a repetition of the experiment (antigen-specific ELISA), which was shown in FIG. 5, with various dilutions of the sera and cross-dilution of the VHH-producing lysate (trans. VHH) and the control lysate (NT). The tetanus immunity can be reproducibly redirected against GFP under various conditions.

EXAMPLES

VHH Production
First a suitable VHH ligand is selected. These targets are used as antigens to immunize a camelid. Preferred organisms for producing VHH fragments in this manner are dromedaries, alpacas or llamas. The protein cocktail comprising the target is injected into the animal. Lymphocytes are isolated from the immunized animal. Then the mRNA is extracted and used to construct a VHH cDNA library. This in turn is used to create a phage display library.

In the phage display, antigen binders with high affinity are selected. The gene sequences of these selected antigen binders are analyzed and synthesized.

Example 1

In one embodiment, a VHH fragment directed against GFP was used. This fragment was published by Martha H. Kubala et al. 2010 (Protein Science, Volume 19, Issue 12, pages 2389 bis 2401).

The c-terminal receptor binding domain of tetanus toxin was used as the protein tag. Thus the amino acid sequence of the example comprises an anti-GFP-VHH and the tetanus toxin domain mentioned. This is Seq ID No. 17:

```
MAQVQLVESG GALVQPGGSL RLSCAASGFP VNRYSMRWYR

QAPGKEREWV AGMSSAGDRS SYEDSVKGRF TISRDDARNT

VYLQMNSLKP EDTAVYYCNV NVGFEYWGQG TQVTVSSEPK

TPKPQPQPQP QPQPNPTTES KCPTSYLSIT FLRDFWGNPL

RYDTEYYLIP VASSSKDVQL KNITDYMYLT NAPSYTNGKL

NIYYRRLYNG LKFIIKRYTP NNEIDSFVKS GDFIKLYVSY

NNNEHIVGYP KDGNAFNNLD RILRVGYNAP GIPLYKKMEA

VKLRDLKTYS VQLKLYDDKN ASLGLVGTHN GQIGNDPNRD

ILIASNWYFN HLKDKILGCD WYFVPTDEGW TNDHHHHHH

Anti-GFP:
Seq ID No. 18:
MAQVQLVESG GALVQPGGSL RLSCAASGFP VNRYSMRWYR

QAPGKEREWV AGMSSAGDRS SYEDSVKGRF TISRDDARNT

VYLQMNSLKP EDTAVYYCNV NVGFEYWGQG TQVTVSSEPK

TPKPQPQPQP QPQPNPTTES KCP

Tetanus toxin:
Seq ID No. 1:
TSYLSIT FLRDFWGNPL RYDTEYYLIP VASSSKDVQL

KNITDYMYLT NAPSYTNGKL NIYYRRLYNG LKFIIKRYTP
```

-continued
```
NNEIDSFVKS GDFIKLYVSY NNNEHIVGYP KDGNAFNNLD

RILRVGYNAP GIPLYKKMEA VKLRDLKTYS VQLKLYDDKN

ASLGLVGTHN GQIGNDPNRD ILIASNWYFN HLKDKILGCD

WYFVPTDEGW TND
```

A schematic illustration of the resulting VHH construct can be taken from FIG. 4. FIG. 3 shows an anti-tetanus antibody that has bonded the VHH constructs with the tetanus toxin tag. In liquids such as blood, plasma or serum, the anti-tetanus antibodies bind to the VHH fragments by way of the protein tag, so that the tetanus immunity is directed against another antigen, in this specific example GFP.

Example 2

10 NMRI mice were immunized with a commercially available tetanus toxin (Tetanol pur, Novartis). Ten additional NMRI mice were handled without immunization as a control group. All mice were held under SPF conditions.

HEK cells were transfected with a plasmid previously described fusion protein containing an anti-GFP VHH and the c-terminal receptor binding domain of tetanus toxin.

Lysates of these transfected cells and control cells were incubated with a pooled serum from the immunized mice and the control mouse.

An ELISA test was performed. The test was performed on plates coated with GST-GFP. The lysate-serum mix was added and the plates were incubated. After a washing step, mouse IgG was detected with an HRP-labeled goat-anti-mouse IgG antibody.

The result of this example is shown in FIG. 5 and FIG. 6.

The mouse IgG from the mice vaccinated against tetanus binds to GFP over the VHH protein tag. The tetanus immunity is now directed against GFP. Thus the redirection of the immune response was successful.

LIST OF SYMBOLS

10 VHH construct
11 VHH fragment/nanobody
12 Protein tag
13 Antibody from a noncamelid species
14 Antibody construct
15 Llama heavy chain antibody
16 Antigen binding site
17 c-terminal receptor binding site of tetanus toxin

---

The invention claimed is:

1. A method for redirecting an immune response of a patient comprising:
    administering a VHH construct comprising:
    a single-domain antibody and a protein tag,
    wherein the protein tag:
    is part of a C-terminal receptor-binding domain of a tetanus toxin according to SEQ ID NO:1, which comprises at least one of SEQ ID NO: 2 to SEQ ID NO:5, or
    wherein the protein tag comprises one or more sequences selected from the group consisting of SEQ ID NO: 6 to SEQ ID NO: 10 and SEQ ID NO: 12 to SEQ ID NO: 16,
    wherein the protein tag is immunogenic and comprises one or more epitopes for binding an antibody known to be present in the patient,
    wherein the size of the protein tag is limited so that only one existing antibody can bind per protein tag, and
    wherein the VHH construct redirects via the antibody known to be present in the patient the immune response of the patient against one or more of the epitopes of the protein tag to an antigen that binds the single-domain antibody.

2. The method according to claim 1, wherein the protein tag comprises at least two of the epitopes.

3. The method according to claim 1, wherein the protein tag is located opposite of an antigen binding site of the single-domain antibody.

4. The method according to claim 2, wherein the one or more epitopes are approximately 8 to 20 amino acids long.

5. The method according to claim 1, wherein the protein tag is a sequence of tetanus toxin.

6. The method according to claim , wherein the protein tag is connected with the VHH single-domain antibody directly or via a linker.

7. The method according to claim 1, wherein the existing antibody that binds the protein tag is a complete immunoglobulin of a non-camelid species.

8. The method according to claim 1, wherein the single-domain antibody is a recombinant single-domain antibody.

9. The method according to claim 1, wherein the VHH construct is produced by a recombinant method.

10. The method according to claim 1, wherein the protein tag generates a polyclonal immune response in vivo in the patient.

11. The method according to claim 1, wherein the existing antibody known to be present in the patient is induced in the patient by vaccination.

12. The method according to claim 1, wherein the immune response is an existing tetanus antibody immune response of the patient and the protein tag consists of one or more of SEQ ID NO: 2 to SEQ ID NO:5.

13. The method according to claim 1, wherein the immune response is an existing tetanus antibody immune response or an existing viral pathogen antibody immune response and the protein tag comprises one or more sequences selected from the group consisting of SEQ ID NO: 6 to SEQ ID NO: 10, SEQ ID NO:12 and SEQ ID NO:13 to SEQ ID NO: 16, respectively.

14. A method for redirecting an existing tetanus antibody immune response of a patient comprising:
    administering a VHH construct comprising:
    a single-domain antibody and a protein tag,
    wherein the protein tag:
    is an immunogenic antigen and comprises one or more epitopes for binding an antibody known to be present in the patient, and
    wherein the protein tag consisting of the amino acid sequence selected from the group consisting of SEQ ID NO: 2 to SEQ ID NO: 12 and is limited in size so that only one antibody can bind the protein tag,
    wherein the VHH construct redirects via the antibody known to be present in the patient the immune response of the patient against one or more of the epitopes of the protein tag to an antigen that binds the single-domain antibody.

15. The method of claim 14, wherein the protein tag is selected from the group consisting of SEQ ID NO: 6 to SEQ ID NO: 12.

* * * * *

UNITED STATES PATENT AND TRADEMARK OFFICE
CERTIFICATE OF CORRECTION

PATENT NO. : 10,772,945 B2
APPLICATION NO. : 15/562901
DATED : September 15, 2020
INVENTOR(S) : Fuener et al.

Page 1 of 1

It is certified that error appears in the above-identified patent and that said Letters Patent is hereby corrected as shown below:

In the Claims

In Column 23, Line 34, in Claim 6, please delete "claim" and insert -- claim 1, --, therefore.

In Column 23, Line 35, in Claim 6, please delete "the VHH single-domain" and insert -- the single-domain --, therefore.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*